United States Patent [19]

Massen

[11] Patent Number: 4,887,155
[45] Date of Patent: Dec. 12, 1989

[54] METHOD AND ARRANGEMENT FOR MEASURING AND/OR MONITORING PROPERTIES OF YARNS OR ROPES

[76] Inventor: Robert Massen, Kämpfenstrasse 39, 7760 Radolfzell, Fed. Rep. of Germany

[21] Appl. No.: 128,715

[22] Filed: Dec. 4, 1987

[30] Foreign Application Priority Data

Dec. 6, 1986 [DE] Fed. Rep. of Germany ....... 3641816

[51] Int. Cl.⁴ .............................................. H04N 7/18
[52] U.S. Cl. ..................... 358/107; 382/18; 364/560; 364/470; 73/158; 250/560
[58] Field of Search ............... 364/560, 563, 562, 725, 364/470; 358/107, 101, 106; 356/383, 385, 384, 387; 73/158, 160; 382/18, 25, 41; 250/562, 560

[56] References Cited

U.S. PATENT DOCUMENTS

| 3,261,967 | 7/1966 | Rosin et al. | 364/560 |
| 3,584,225 | 6/1971 | Lindemann et al. | 250/562 |
| 4,338,565 | 7/1982 | Hall | 73/158 X |
| 4,415,926 | 11/1983 | Henry | 358/107 |
| 4,511,253 | 4/1985 | Glöckner et al. | 250/560 X |
| 4,586,372 | 5/1986 | Massen | |
| 4,731,860 | 3/1988 | Wahl | 364/725 X |
| 4,744,035 | 5/1988 | Hashim | 358/107 X |

Primary Examiner—James J. Groody
Assistant Examiner—Victor R. Kostak
Attorney, Agent, or Firm—Sixbey, Friedman, Leedom & Ferguson

[57] ABSTRACT

For measuring and/or monitoring properties of yarns or ropes with the aid of an image sensor a two-dimensional image of a portion of the yarn or rope is acquired and converted to electrical image signals. The image signals are digitized in image point manner and stored in an image signal memory at memory locations assigned to the image points. By a calculating unit the values of the properties to be detected are determined from the stored digital image signals. The properties which can be measured and/or monitored in this manner are in particular the diameter of the yarn or rope, the statistical values of projecting fibres, filaments or wires and the twist of the yarn or rope.

21 Claims, 7 Drawing Sheets

METHOD AND ARRANGEMENT FOR MEASURING AND/OR MONITORING PROPERTIES OF YARNS OR ROPES

TECHNICAL FIELD

The invention relates to a method of measuring and/or monitoring properties of yarns or ropes, and an arrangement for carrying out the method.

BACKGROUND OF THE INVENTION

According to present-day terminology the term "yarns" covers both simple spinning fibre yarns which are made in a spinning machine by twisting spinning fibres and also twisted yarns which are made by twisting two or more single yarns. Ropes or cables are made by turning or plaiting a plurality of strands which in turn can be turned or plaited from a plurality of yarns. In the special case of metal cables (wire ropes) the basic components are not spinning fibres but wires.

In the production and processing of yarns and ropes various properties must be measured or monitored as far as possible continuously. These include in particular the following properties:
1. the diameter (the thickness) and the fluctuations thereof;
2. the unroundness (deviation from the circular form) and the fluctuations thereof;
3. the frequency and size of projecting individual filaments or wires;
4. the average number of twists or turns per unit length and the fluctuations thereof;
5. the elongation, which can be derived from the change of the number of twists per unit length.

In yarns, these parameters are not only responsible for the quality of the textiles made with these yarns but also for a number of subsequent working processes. For example, the dye absorption depends on the number of twists per unit length. Fluctuations of this parameter cause visible and disturbing fluctuations in colour shades, in particular with plastic yarns.

In the case of ropes monitoring these parameters makes it possible to increase reliability and detect aging processes at an early stage. This is particularly important in conveying apparatus for transporting persons, for example in mining. In the case of many technical yarns and ropes the elongation must be continuously determined. The determination of the frequency and size of projecting filaments or wires is an indication of filament or wire breakages which impair the strength.

Various methods and arrangements are known with which in each case one of the above parameters can be measured or monitored, although usually under restrictive conditions. Thus, capacitive methods are known for monitoring the thickness fluctuations of yarns in which the yarn to be tested lies between the electrodes of a capacitor and thus forms part of the dielectric. These capacitive methods operate contactless and without destruction and are also suitable for monitoring moving yarns. Such methods cannot however measure the twisting, projecting filaments or unroundness. They are moreover sensitive to disturbing influences, such as moisture and density changes, and they fail in the case of metal materials. Furthermore, the measurement of relatively large diameters, for example as occur in ropes, can be made only with difficulty.

So far, the problem which has been solved in the least satisfactory manner is that of determining the number of twists or turns per unit length. For this purpose purely mechanical systems exist in which a yarn specimen is clamped and untwisted until the individual fibres or filaments lie in parallel. Another known apparatus in which with the aid of a punctiform optical measuring head the number of twists per unit length is determined on a yarn specimen is also only a laboratory measuring instrument for evaluating short yarn specimens and not a process data acquisition apparatus for continuous use with running yarns in their production or processing, let alone for monitoring ropes in operation. For monitoring some properties of metal ropes electromagnetic methods also exist but they cannot detect all the parameters of interest and are of course not suitable for non-metallic yarns or ropes.

A further disadvantage of the methods hitherto used for measuring the twisting of running yarns or ropes is that from the running yarn or rope a time signal must be derived and consequently the speed is incorporated into the method. The exact determination of the speed is however not possible in slip-free manner with the usual mechanical means, for example a pulley. For this reason it is also not possible with these known methods to determine the number of twists per unit length and the elongation exactly and independently of the speed. To overcome this disadvantage it is also known to apply markings to the measured object. Thus for example shaft conveying ropes are frequently provided with counting wires which are twisted into the wire cable so that they can be followed from the outside. The attachment of such markings is however restricted to a few specific cases.

SUMMARY OF THE INVENTION

An object of the invention is the provision of a method with which the previously mentioned properties of stationary or moving yarns or ropes can be continuously measured or monitored with great accuracy in contactless manner without destruction or markings in the production, processing and/or use.

According to the invention this object is achieved in that with the aid of an image sensor a two-dimensional image of a portion of the yarn or rope is picked up and converted to electrical image signals, that the image signals are digitized in image point manner and stored in an image signal memory at memory locations associated with the image points, and that by a calculating unit the values of the properties to be determined are derived from the stored digital image signals.

The method according to the invention makes it possible to determine several data of interest of the yarn or rope with a single measuring apparatus. Since these data can be obtained from a digitally stored two-dimensional image of the yarn or rope it is of no consequence whether this image was picked up from a stationary yarn or rope or one moving with a speed of any magnitude. The image is picked up contactless without the yarn or rope being affected thereby in any manner. The stored digital image signals of a two-dimensional image can be evaluated by a calculating unit in a very short time in a continuous evaluation of two-dimensional images picked up consecutively at short intervals of time is possible. This permits practically continuous measurement and monitoring of the properties of the yarn or rope. By continuously comparing the measured values derived from the consecutive images it is further possible to determine changes or fluctuations of the properties monitored. The evaluation of the stored digital image signals by a calculating unit, preferably a suitably programmed computer, makes the method very flexible and adaptable to different yarns and ropes. Furthermore, by the choice of the illumination, the radiation used for the illumination and the image sensor used to convert the radiation to electrical image signals the method can be adapted in optimum manner to a great variety of operating conditions.

BRIEF DESCRIPTION OF THE DRAWINGS

Further features and advantages will be apparent from the following description of examples of embodiment with the aid of the drawings, wherein.

DETAILED DESCRIPTION OF PREFERRED EMBODIMENTS

Figure 1:
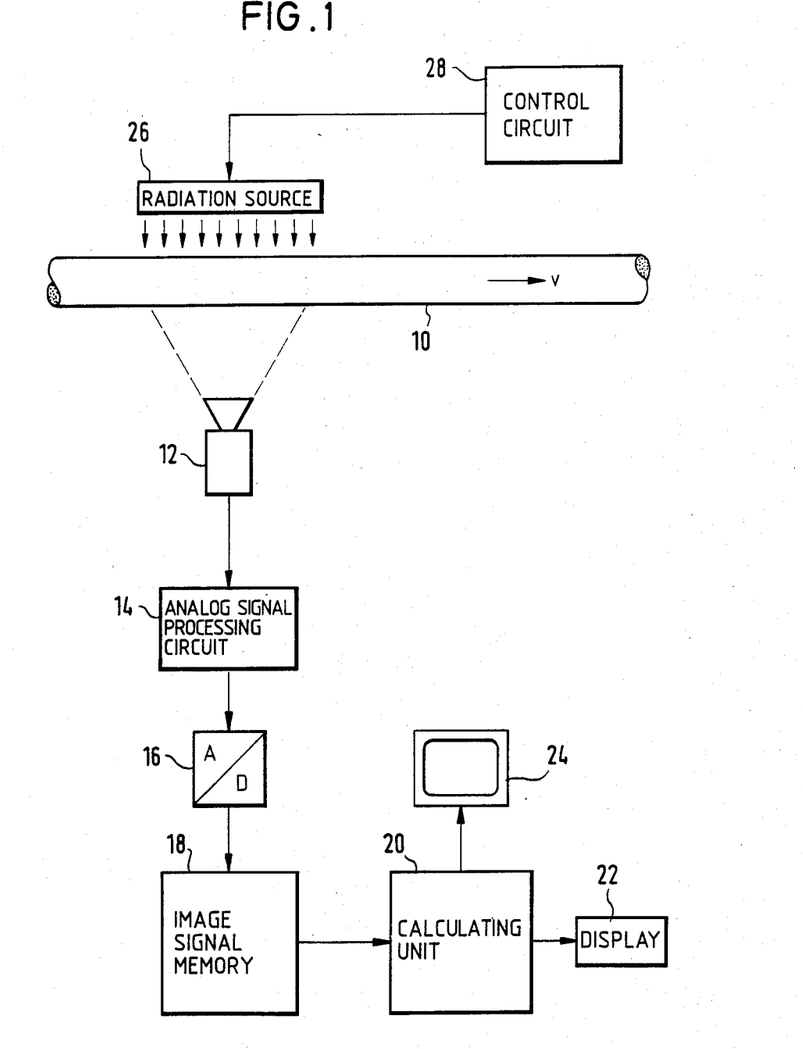
FIG. 1 is a schematic diagram of an arrangement for measuring and/or monitoring properties of yarns or ropes.

The arrangement for measuring and/or monitoring various properties of a yarn or rope 10 shown in FIG. 1 includes an image sensor 12 which picks up the image of a portion of the yarn or rope 10 and converts it to an analog electrical image signal which is emitted at its output. The image sensor 12 may be a television camera which scans the image to be picked up line-by-line in a television scan so that the output signal is a conventional video signal. However, instead of a television camera standard-free matrix sensors may be used, for example CCD semiconductor matrix cameras. In each case the image sensor 12 must be able to convert a two-dimensional image of the portion of the yarn or rope 10 lying in the field of view to an electrical image signal.

The analog image signal furnished by the image sensor 12 is supplied after the necessary analog processing in an analog signal processing circuit 14 to an analog-digital converter 16 in which it is digitized. When the analog image signal is a television video signal the analog-digital converter 16 derives from the analog image signal periodic sample values and converts each sample value to a digital signal. Each sample value corresponds to an image point (pixel) on a scanning line of the television image and its amplitude corresponds to the brightness value (grey value) of the image point. In the analog-digital converter 16 the sampled amplitude value is quantized and for example converted to a binary code group which reprsents the brightness value in the form of a binary number. The position number of the binary number, i.e. the bit number of the code group, depends on the desired quantization resolution.

If the image sensor 12 is a matrix camera the analog image signal itself may consist of discrete analog signal values, each of which is associated with an image point of the matrix. The digital-analog converter then converts each analog signal value directly to a digital signal which represents the brightness value of the respective image point.

In each case the digital output signals of the analog-digital converter 16 are entered into a highspeed image signal memory 18 which for each image point of a two-dimensional image picked up by the image sensor 12 has a memory location at which the complete digital signal of the respective image point can be stored Connected to the read output of the image signal memory 18 is a calculating unit 20, which is for example a microcomputer. The calculating unit 20 can call up the digital image signals stored in the image signal memory 18 and, in a manner to be explained below, determine therefrom the values of the properties of the yarn or rope to be measured or monitored. The values determined can be displayed in a display device 22 or output in any other manner known per se, for example by means of a printer connected to the calculating unit 20. Furthermore, a monitor 24 can be connected to the calculating unit 20 and on said monitor the image picked up and stored in the image signal memory 16 can be displayed for checking by an operator.

When the two-dimensional image stored in the image signal memory 18 has been completely evaluated by the calculating unit 20 the next image picked up by the image sensor 12 can be entered in digitized form into the image signal memory 18 and evaluated. In this manner continuous monitoring of the yarn or rope 10 is possible. This is advantageous in particular when the yarn or rope 10 is moving in its longitudinal direction past the image sensor 12 as indicated by an arrow v in FIG. 1.

To obtain a sharp image even with high feed speeds it is expedient to illuminate very briefly with a strong radiation source 26 the portion of the yarn or rope 10 to be picked up. A control circuit 28 synchronizes the illumination with the acquisition by the image sensor 12. With repeated image acquisitions for continuous measurement or monitoring the brief illumination may be carried periodically in the manner of a stroboscope. The acquisition may be with visible light and the radiation source 26 may then be an electron flash. To obtain images of the structure independent of the colouring of yarns an illumination in the infrared range may be expedient. The dyes used normally in the textile industry are so devised that they reflect in particular in the visible range of the spectrum. In the near infrared range the dyes are transparent. It is therefore possible with infrared illumination to obtain similar images of the structures of very differently dyed yarns, from white through coloured up to deep black yarns.

For the illumination it is also possible to use wavelengths which are still further outside the visible spectrum than the infrared range, e.g. X-ray radiation for obtaining grey value images of metal ropes. Finally, radiation other than electromagnetic radiation may also be used, for example ultrasonic waves. In each case of course an image sensor adapted to the radiation type and wavelength must be used. For example, to render X-ray radiation visible video cameras may be used in conjunction with image converters. However, semiconductor cameras also exist which generate a video signal directly from the X-rays. The state of the art in medicine includes rendering ultrasonic images visible.

The image may be picked up in incident light so that the image sensor 12 receives the light reflected by the yarn or rope or, as illustrated in FIG. 1, in counter light so that the image picked up is produced by the radiation allowed to pass by the yarn or rope. The type of illumination used depends on the nature of the yarn or rope to be investigated and on the radiation used.

A particular advantage of the arrangement illustrated in FIG. 1 resides in that from the digital image signals of a single two-dimensional image stored in the image signal memory 18 the calculating unit 20 can determine at the same time several different properties of the yarn, that is in particular:

1. the diameter (the thickness);
2. the number of twists per unit length (meter or inch), in the case of yarns also referred to as "twist number" or "twist coefficient", whereas for ropes generally the reciprocal is given, i.e. the length of a twist as "turn height" or "lay length";
3. the "hairiness" i.e. the number and size of the filaments or wires projecting from the surface.

By comparing the measured values obtained from several consecutively taken images of a moving yarn or rope it is then possible to detect changes or fluctuations in these properties.

Figure 2:
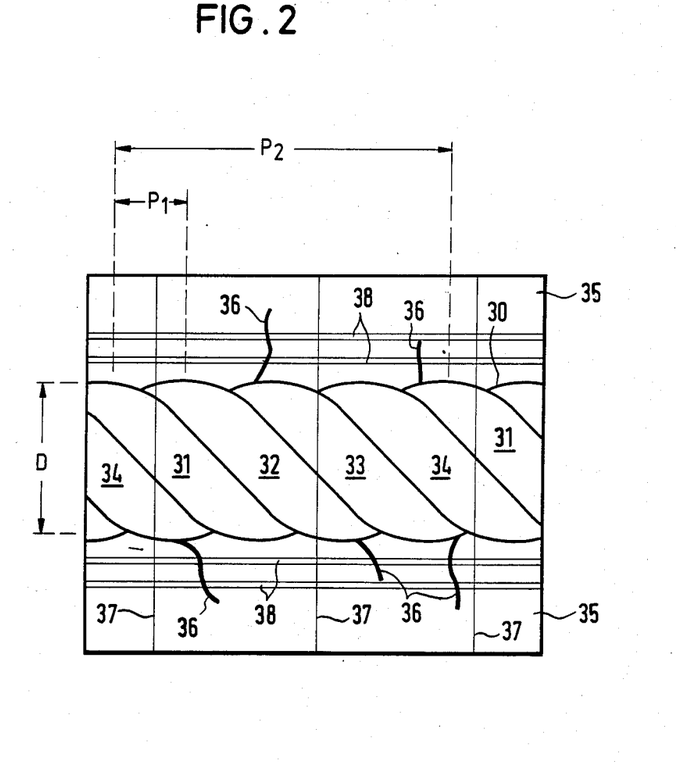
FIG. 2 shows the image of a portion of a yarn or rope picked up with the image sensor of the arrangement of FIG. 1.

With the aid of FIG. 2, which shows an image taken with the arrangement of FIG. 1, it can be explained how these different properties can be measured or monitored. The image area contains the image of a portion 30 of the yarn or cable 10 picked up and an image of the background 35 on either side thereof. The illustration corresponds to a twisted yarn twisted from four individual yarns 31, 32, 33, 34 or a rope twisted from four strands. Individual filaments or wires 36 which project from the surface of the yarn or rope stand out against the background.

The measurement of the diameter D does not involve any particular problems. The calculating unit can either count the number of image points belonging to the image of the yarn or rope along several transverse lines 37 extending perpendicularly to the longitudinal axis of the yarn or rope or it can determine the ratio of the total number of image points belonging to the image of the yarn or rope to the total number of the image points of the image area picked up. In both cases the mean diameter D can easily be calculated on the basis of the known imaging scale of the image sensor 12. The image points belonging to the yarn or rope are apparent from the different brightness values compared with the image points of the background.

However, it is not as easy to determine the twist either as number of twists per unit length (twist number, twist coefficient) or as axial length of a twist (turn height, lay length). The arrangement of FIG. 1 offers various possibilities for determining the twist from the stored digital image signals; a preferred method is to evaluate the periodic structure of the yarn or cable. This method is based on the fact that each yarn or cable because of the twisting of its components has a periodic structure. This is particularly pronounced in twisted yarns or ropes. As apparent from the illustration of FIG. 2 a distinction can be made in this case between two periods:

(a) a fundamental period $P_1$ which is defined by the mean distance, measured in the axial direction, between two consecutive individual yarns or strands;

(b) a twist period $P_2$ which is defined by the distance between two consecutive turns of the same single yarn or the same strand. The twist period $P_2$ is thus equal to the turn height or lay length, the reciprocal of which is the twist number.

There is a clear relationship between the two periods $P_1$ and $P_2$: the twist period $P_2$ corresponds to the product of the fundamental period $P_1$ and the number of twisted individual yarns or strands. Thus, to obtain the desired measured value it suffices to determine one of these two periods.

The calculating unit 20 determines the desired period in the longitudinal direction from the digital image signals stored in the image signal store 18 by employing a suitable computing method.

A preferred method for determining the desired period in the longitudinal direction of the yarn or rope is the formation of a unidimensional similarity function of stored digital image signals originating from at least one image point row extending in the longitudinal direction. A particularly suitable unidimensional similarity function is the autocorrelation function. As is known, the autocorrelation function (in short: ACF) is the correlation of a function with the same function displaced a variable amount as a function of the mutual displacement. In the present case involving stored image signals the function is defined by the brightness values of consecutive image points of the evaluated image point row. The consecutive image points lie in the image at uniform intervals $\Delta x$ apart each corresponding to a distance $\Delta X$ on the yarn or rope defined by the imaging scale of the image sensor. The entire image point row includes M image points. If the first image point of the image point row is designated image point No. 1 and has the coordinate $x = 0$, the image point No. $(i+1)$ has the coordinate $i \cdot \Delta x$ and the image point No. M has the coordinate $(M-1) \cdot \Delta x$.

The autocorrelation function $R_{xx}(k)$ is defined by the sum of the pairwise products of the brightness values of image points of an image point row with the brightness values of image points of the same image point row displaced by k:

$$R_{xx}(k) = \sum_{i=0}^{L-1} I(i \cdot \Delta x) \cdot I((i+k) \cdot \Delta x) \quad (1)$$

with $k = 0, 1, 2, \ldots, (Q-1)$

Wherein:

$I(i \cdot \Delta x)$: is the brightness value (grey value) of the image point with the coordinate $i \cdot \Delta x$;

L: is the number of the image point pairs processed for one value of the displacement operator k;

Q: is the number of calculated support values of the autocorrelation function.

For each value of the displacement operator k in accordance with equation (1) a support value of the autocorrelation function is obtained, i.e. a total of Q support values. Thus, for example for an image point row the autocorrelation function shown in the diagram of FIG. 3 results. The autocorrelation function is not continuous but made up pointwise, each point corresponding to a support value. For certain values of k the support values have maxima because maximum coincidence is obtained with the corresponding mutual displacements $k \cdot \Delta x$ due to the fundamental period $P_1$ of the structures compared. To increase the statistical accuracy the autocorrelation functions of several selected image point rows or of all image point rows belonging to the image portion of the yarn or rope may be summated.

If the image sensor 12 is a television camera it is convenient to align said camera so that the axis of the image of the yarn or rope lies parallel to the line direction of the television scan raster because the image point rows to be evaluated then correspond to the scanning lines. This facilitates the addressing of the image signals stored in the image signal memory 18 but it is not absolutely essential. A particular advantage of the evaluation of stored image signals of a two-dimensional image is precisely that the image signals can be called up and processed independently of the time sequence of their formation.

Figure 3:
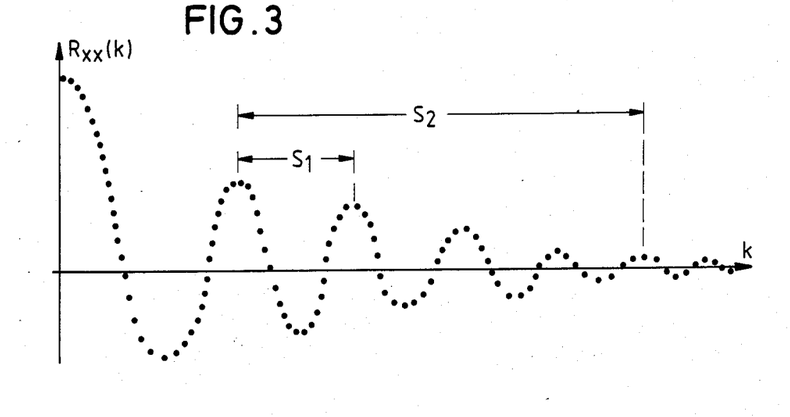
FIG. 3 is a diagram of an autocorrelation function which is obtained with an embodiment of the method which can be carried with the arrangement of FIG. 1.

The distance $S_1$ between two consecutive maxima of the autocorrelation function in the diagram of FIG. 3 corresponds to the fundamental period $P_1$ of the yard or rope illustrated in FIG. 2 and the distance $S_2$ between four consecutive maxima corresponds to the twist period $P_2$, i.e. directly to the turn height or lay length, the reciprocal of which is the twist number, i.e. the number of twists per unit length. The distance $S_1$ corresponds to a specific number $n_1$ *of image point intervals $\Delta x$ and the distance $S_2$* corresponds to a specific number $n_2$ of image point intervals $\Delta x$. Due to the relationship defined by the imaging scale between the image point interval $\Delta x$ and the corresponding distance $\Delta X$ on the yarn or rope the turn height or lay length is then directly $n_2 \cdot \Delta X$.

Instead of the autocorrelation function other similarity functions may be used to determine the desired periods $P_1$ and $P_2$. Since to calculate the autocorrelation function products of the stored brightness values must be formed a considerable time and hardware expenditure is necessary. A similarity function which is simpler to calculate is the sum of the amount differences of the mutually displaced brightness values:

$$D_{xx}(k) = \sum_{i=0}^{L-1} |I(i \cdot \Delta x) - I((i + k) \cdot \Delta x)| \quad (2)$$

with $k = 0, 1, 2, \ldots, (Q - 1)$

The various letters here have the meanings given for equation (1).

Figure 4:
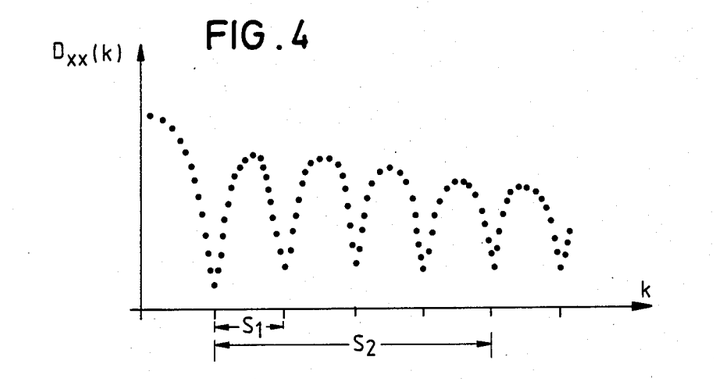
FIG. 4 is a diagram of another similarity function which is obtained with another embodiment of the method which can be carried out with the arrangement of FIG. 1.

The similarity function $D_{xx}(k)$ provides basically the same information as the autocorrelation function $R_{xx}(k)$ but can be determined with less effort. FIG. 4 shows the typical profile of the similarity function $D_{xx}(k)$ for a two-dimensional imge of the yarn or rope. The fundamental period $P_1$ or the twist period $P_2$ corresponding to the turn height or lay length can be defined most accurately from the periodic minima because they are more distinctly pronounced than the maxima.

Figure 5:
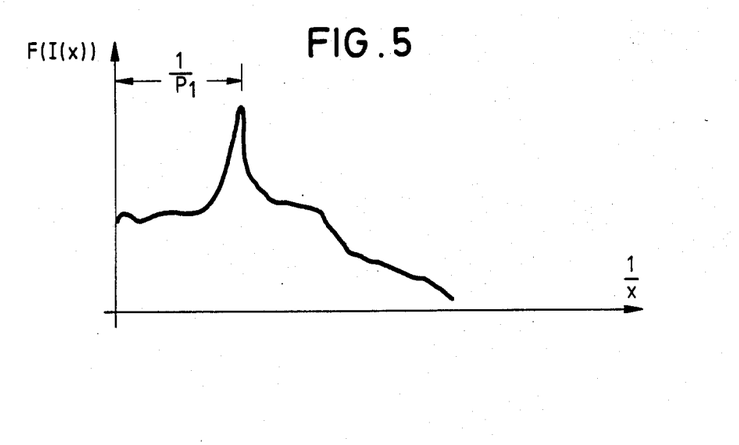
FIG. 5 is the diagram of a spectral transformation which is obtained with a further embodiment of the method which can be carried out with the arrangement of FIG. 1.

Instead of using a similarity function, the desired periods of the structure of the yarn or rope can also be determined from the maximum of a spectral transform of the digital image. This can be done by using the Fourier transform or an orthogonal transform related thereto, the Walsh transform or the Hadamard transform. Since fast algorithms are known for many of these transforms (e.g. the fast Fourier transform algorithm), using them can result in a saving in time, in particular in the calculation by microcomputer. In this case the fundamental period $P_1$ is obtained from the dominant maximum of the spectrum as illustrated in FIG. 5 for the Fourier transformed $F(I(x))$. Since the autocorrelation function and the Fourier transform represent transform pairs, they both contain the same information although in a different representation.

The determination of the twist number or the turn height from the periodic structure according to one of the previously described methods is not restricted to test specimens which are twisted yarns or ropes with very pronounced structure. A so-called simple yarn or spinning fibre yarn which consists of a number of spinning fibres held together by twisting (spinning) also has a periodic structure when the staple length of the twisted spinning fibres is greater than the turn length of a twist. The periodic structure then results from the fact that the same spinning fibres appear in the image several times in each case at the interval of the turn height. The previously described methods are very sensitive for such periodicities, although they are only weakly pronounced. In this case the fundamental period $P_1$ coincides with the twist period $P_2$, i.e. the distance between two consecutive maxima of the autocorrelation function of FIG. 3 or between two minima of the similarity function of FIG. 4 correspond directly to the turn height.

Finally, in a twisted yarn or rope with pronounced periodic structure which also occurs at the edges of the imaging (FIG. 2) the period. can also be determined by evaluating the grey value silhouette in that the maxima, or still better the more sharply pronounced minima, of the silhouette are detected by comparison with the brightness values of the background and the distance between two maxima or minima measured directly. This method cannot however be applied to simple spinning fibres yarns.

Figure 6:
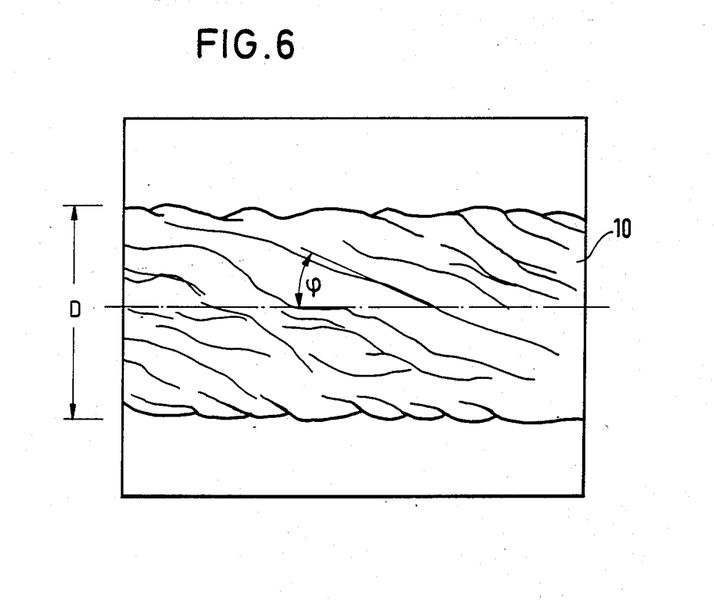
FIG. 6 shows the image of a portion of a yarn picked up with the image sensor of the arrangement of FIG. 1 with highly disturbed fibre alignments of no periodic structure.

However, yarns made from individual spinning fibres, in particular rotor-spun yarns made in turbulent air flow, exist in which the individual fibres are so turbulently tangled that a periodic twisting is no longer apparent. FIG. 6 shows the image of such a yarn with highly disturbed fibre alignment taken with the arrangement of FIG. 1. In such yarns in some cases a twisting in the true sense no longer even exists. The term "twist per unit length" must in this case be extended to a statistical parameter which can still be measured.

A statistical parameter which can still be measured and can be obtained with the arrangement of FIG. 1 from the digital image signals stored in the image signal memory 18 is the mean fibre angle $\phi$ of the individual fibres with respect to the yarn axis. In yarns with highly disturbed fibre alignments, as in yarns rotor-spun in turbulent air flow, the mean fibre angle $\phi$ provides measuring information which represents a physically logical generalization of the term "twist per unit length" and can be used like the latter to assess the quality.

Figure 7:
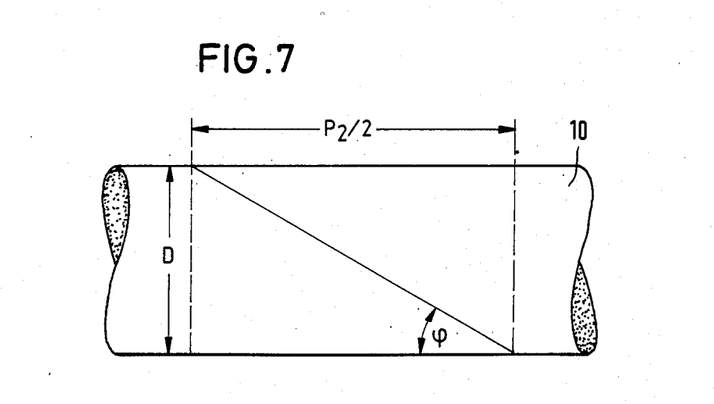
FIG. 7 is a diagram to explain the determination of the twist per unit length from the mean fibre angle in a yarn of the type shown in FIG. 6.

When the diameter D of the yarn has been determined in the manner previously described the "twist period" according to FIG. 7 can be calculated from the mean fibre angle $\phi$ of the yarn 10 in accordance with the following equation:

$$Phd \, 2 \, 32 \, 2 \cdot D/tg\phi \tag{3}$$

The desired fibre angle $\phi$ can be determined only from the surface structure of the yarn which is best visible under lateral incident light. Since said surface structure is difficult to see because of irregularities of the surface, projecting fibres, reflections or the like, the image of the yarn surface stored digitally in the image signal memory 18 is processed by known methods of image processing to eliminate or at least reduce these disturbances and to emphasize the edges. The image thus processed serves as basis for the determination of the fibre angle.

When preparing the image stored in the form of digital image signals the fact that the fibre angle to be expected can lie only in a predetermined range is utilized. Consequently, the disturbances can be greatly reduced by filtering out the disturbing directions.

The filtering is preferably done by differentiating in three directions, that is in the x direction parallel to the yarn axis, in the y direction perpendicular to the yarn axis and in the direction of the minor diagonal (x-y direction). Differentiating in a direction results in the edges extending in this direction being filtered out whilst other edges, in particular the edges extending perpendicular to said direction, are emphasized. After the filtering the desired direction is predominant.

The differentiating also effects at the same time a highpass filtering so that fine structures and edges stand out whilst large-area structures and illumination fluctuations are suppressed or at least weakened.

The differentiating in a direction is effected in that the digitally stored image is shifted by one image point (1 pixel) in the differentiating direction and the brightness value of each image point of the displaced image is subtracted from the brightness value of the associated image point of the undisplaced image. The result of each subtraction is then the brightness value of an image point of the differentiated and filtered image. Each subsequent differentiation proceeds from the differentiated image obtained by the previous differentiation.

If the digitally stored brightness value of the image point having the coordinates x and y is denoted by I(x,y), the differentiated and filtered image is obtained in the following steps:

1. Differentiation in the x direction:

$$I_1(x,y) = [I(x,y) - I(x+1,y)] + K \tag{4}$$

$I_1(x,y)$ is the brightness value of the image point having the coordinates x and y in the image differentiated in the x direction.

2. Differentiation in the y direction:

$$I_2(x,y) = [I_1(x,y) - I_1(x,y+1)] + K \tag{5}$$

$I_2(x,y)$ is the brightness value of the image point having the coordinates x and y in the image differentiated in the x direction and in the y direction.

3. Differentiation in the x-y direction:

$$I_3(x,y) = [I_2(x,y) - I_2(x+1,y+1)] + K \tag{6}$$

$I_3(x,y)$ is the brightness value of the image point having the coordinates x and y in the image differentiated in all three directions.

The constant K added in each step ensures that only positive differential images are formed and thus a signless further processing is achieved. To increase the value range of the differential images a multiplying factor may also be assigned to the terms (4) to (6).

The digital image obtained after the third step is then used as basis to determine the fibre angle $\phi$. For this purpose various methods are suitable.

Some methods for determining the fibre angle require a binarized image, i.e. an image in which the brightness value of each image point is represented by a single bit which has either the binary value 0 (black) or the binary value 1 (white). If necessary, the differentiated and filtered image obtained by the above method is binarized in that the digital brightness value of each image point is compared with an entered binarizing threshold; when the brightness value exceeds the binarizing threshold the image point is assigned the binary value 1 and otherwise the binary value 0.

Three methods have proved particularly suitable for the determination of the fibre angle $\phi$:

correlation;
Hough transformation;
vector rotation

These three methods will be explained in detail below.

Correlation

For correlation the filtered image obtained by the aforementioned method is used, i.e. without binarizing. Two image lines are displaced with respect to each other and for each value of the displacement operator a measure of the coincidence is calculated. The maximum of the correlation function thus obtained is sought. From the value of the displacement operator at which the maximum occurs and at the interval of the two correlated image lines the desired fibre angle $\phi$ can be calculated.

The smaller the distance between the two image lines the more reliable the correlation but on the other hand the less the accuracy of the calculated angle. For this reason intermediate values of the correlation function obtained are necessary which can be recovered by a spline interpolation.

In a practical case two image lines are correlated with an interval of three image lines. Firstly the mean value $I_m$ of the brightness values of the first image line is formed. Then the two image lines are displaced within the measuring window each by one image point and for each value of the displacement operator k between for example 0 and 15 image points a support value of the correlation function $R_{xy}(k)$ is calculated:

$$R_{xy}(k) = \sum_{i=0}^{L-1} [I_3(x_i, y) - I_m] \cdot [I_3(x_{i+k}, y+3) - I_m] \tag{7}$$

In this equation L is the number of image points of an image line lying in the measuring window.

Firstly the maximum is sought from the 16 correlation support values. In the interval between the maximum and the next smallest value by interpolation with a spline function intermediate values are formed and with the aid of said spline interpolation the actual maximum in this interval is determined to obtain the fibre angle $\phi$ with adequate accuracy. From the interval $\Delta y$ of the correlated image lines and the displacement $k_{max}$ at which the maximum occurs the fibre angle $\phi$ is then calculated in accordance with the following equation:

$$\phi = \text{arctg}(\Delta y / k_{max}) \tag{8}$$

Hough Transformation

The Hough transformation is a method by which colinear image points are discovered. The mathematical basis is the representation of a straight line in the Hesse standard form:

$$r = x \cdot \cos \alpha + y \cdot \sin \alpha \tag{9}$$

Figure 8:
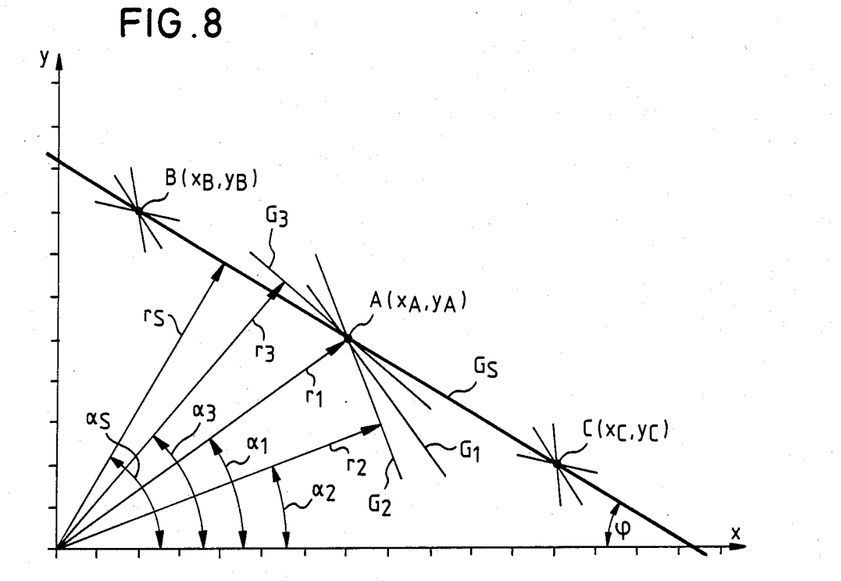
FIG. 8 is a diagram to explain the determination of the mean fibre angle by a Hough transformation.

In this equation r is the distance of the coordinate origin from the straight line measured on the normal passing through the coordinate origin and $\alpha$ the angle between the x axis and said normal. This is shown in FIG. 8 for a straight line $G_1$, the intersection between the straight line and the normal passing through the origin being denoted by A. If the coordinates $x_A$, $y_A$ of the point A are known the constants $r_1$ and $\alpha_1$ of the Hesse normal form associated with the straight line $G_1$ can easily be calculated from the above equation (9). The value pair $r_1$, $\alpha_1$ corresponds to a point in an $r-\alpha$ diagram shown in FIG. 9. Each point in said $r-\alpha$ diagram corresponds to a straight line uniquely defined in the x-y coordinate system of FIG. 8 by the Hesse normal form. By simple trigonometrical relationships the associated value pairs r, $\alpha$ can be calculated for other straight lines passing through the point A and entered in the r-$\alpha$ diagram. For this purpose for example the angle $\alpha$ is changed in each case by 5° and the associated origin distance r calculated. The points thus calculated lie on a curve $K_A$ which represents the sheaf of lines passing through the point A. As example in FIG. 8 two further straight lines $G_2$, $G_3$ of said sheaf of lines is represented having the associated parameters $r_2$, $\alpha_2$ and $r_3$, $\alpha_3$ respectively and in FIG. 9 the associated points on the curve $K_A$ are indicated.

To determine the fibre angle $\phi$ in the selected image fragment of the filtered and binarized image white image points are searched for; for each of said points the associated coordinate values x, y are known. Thus, in accordance with the method set forth above the values r, $\alpha$ of the sheaf of lines passing through the image point can be determined and all these value pairs can then be represented as curve in the r-$\alpha$ diagram. As example in FIG. 8 in addition to the image point A two further image points B and C are shown and in FIG. 9 the associated curves $K_B$, $K_C$.

Figure 9:
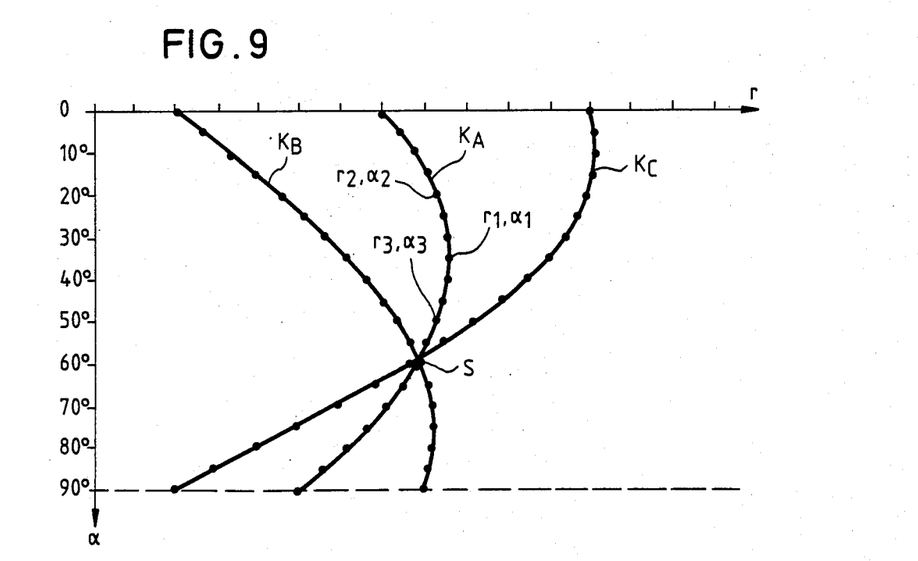
FIG. 9 is a further diagram to explain the determination of the mean fibre angle by a Hough transformation.

If two curves intersect in the r-$\alpha$ diagram of FIG. 9 the point of intersection corresponds to a straight line which passes through the two associated image points in the coordinate system of FIG. 8. If a great number of such curves intersect at the same point or at least in a narrow region all the associated image points are colinear. Thus, the common intersection point S in the r-$\alpha$ diagram of FIG. 9 corresponds in the coordinate system of FIG. 8 to the straight line $G_S$ with the value pair $r_S$, $\alpha_S$ passing through the three image points A, B and C.

If such a common straight line $G_S$ is established for a large number of white image points there is a high probability that these image points will belong to the same fibre. Since the x direction of the coordinate system corresponds to the direction of the yarn axis the angle between the straight line $G_S$ and the x axis is the desired angle $\phi$. Said fibre angle can be derived directly from the diagram of FIG. 9 because it is the complement of the angle $\alpha_S$ in the right-angled triangle:

$$\phi = 90° - \alpha_S \tag{10}$$

A probable fibre angle is thus determined. The same operation is repeated for further image point rows in various image fragments.

Vector Rotation

A requirement for determining the fibre angle by vector rotation is once again a binarized image. The principle is that of turning a vector between 0° and 90° in 1° steps and in each case counting the white image points lying thereon. The sum of the image points lying on the vector is a measure of its emphasis. Thereafter a histogram is output of the number of image points present for each angle. Several measurements are carried out over the entire image, the number thereof depending on how dense the white image points lie in the x direction. Finally a sum histogram of the measurements is output. The maximum of this function gives the desired mean fibre angle.

In each of the cases outlined above after determining the greatest possible number of fibre angles the histogram is formed, i.e. the frequency distribution of the fibre angles determined. This histogram is subjected to suitable known statistical smoothing and interpolation methods and in its entirety provides representative information on the mean twist of the spun individual fibres and their uniformity. This representation can be reduced to a few parameters of the histogram, such as mean value, most frequent value, dispersion of the fibre angles, etc., if the entire profile of the histogram is not required for the assessment. These processing steps can be carried out simultaneously with the digital image evaluation by the image computer.

Figure 10:
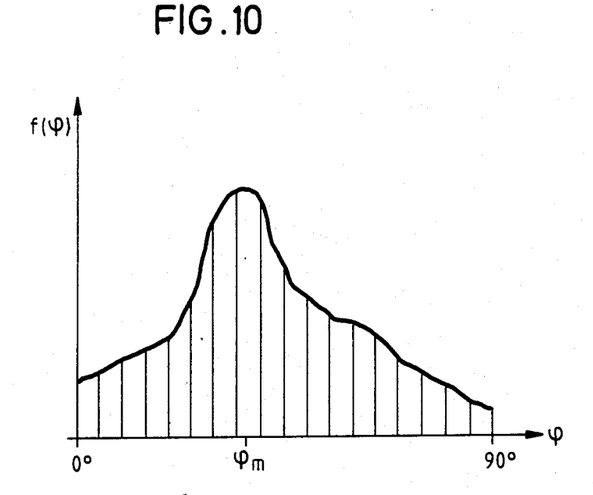
FIG. 10 is a histogram of the fibre angles determined with pronounced maximum.

As an example in FIG. 10 the histogram of the frequency $f(\phi)$ is represented as a function of the fibre angle determined. The angle $\phi_m$, which was determined with maximum frequency, corresponds to the dominant fibre direction.

Figure 11:
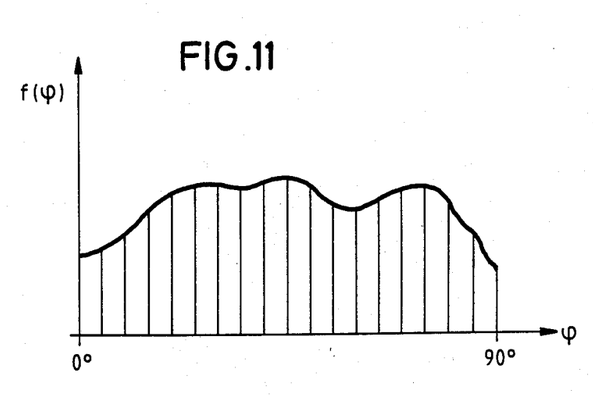
FIG. 11 is a histogram without pronounced maximum unsuitable for the evaluation and FIG. 12 is a schematic diagram of a measuring arrangement with three image sensors for determining the roundness of a yarn or rope.

With individual fibres subjected to pronounced turbulence local areas are present on the yarn surface at which such a dominant fibre direction does not exist. This manifests itself in an equally distributed histogram without typical maximum as shown in FIG. 11. By monitoring the maximum of the histogram such yarn areas, not suitable for the measurement, can be automatically rejected.

FIG. 2 also shows how the "hairiness" can be determined by the calculating unit 20. Outside the image of the yarn or rope 10 in one or more imaginary test strips 38 extending parallel to the axis of the yarn or rope the image points of projecting filaments or wires occuring in the test strip are detected on the basis of the different brightness values compared with the brightness values of the background and counted. Each test strip can for example correspond to an image point row or to several adjacent image point rows. By carrying out the detection in a plurality of parallel test strips information can be obtained not only on the frequency but also on the length of the projecting filaments or wires.

Figure 12:
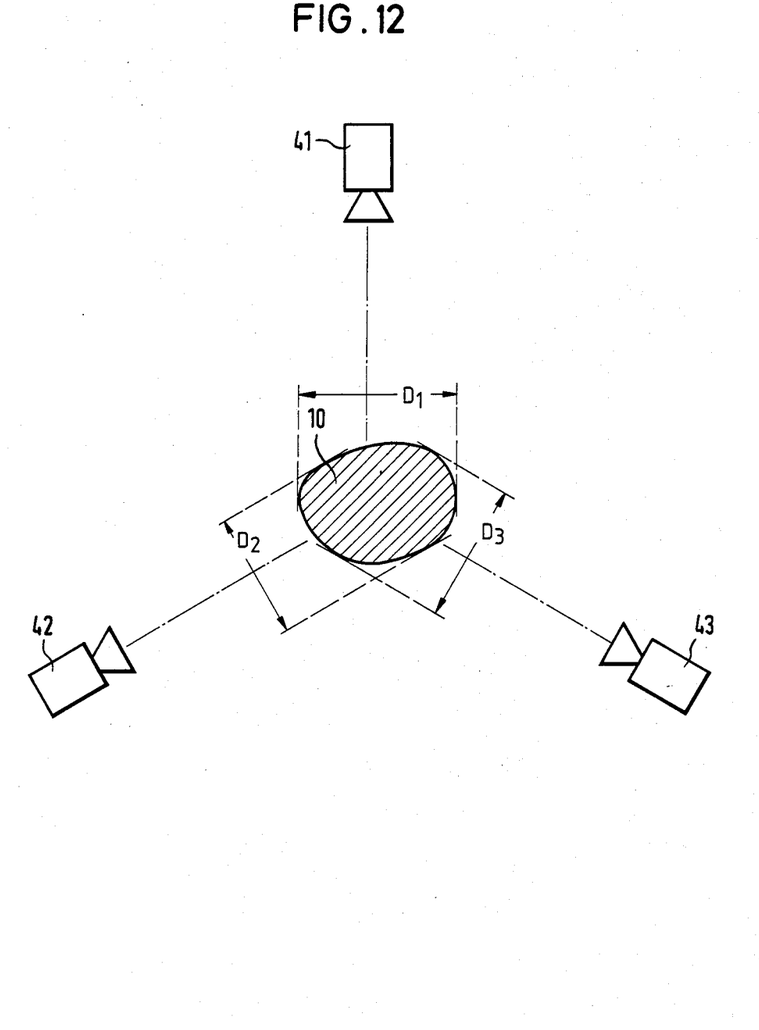

Finally, FIG. 12 shows how by providing several image sensors the spatial silhouette of the yarn or cable can be detected and information thereby obtained on the three-dimensional geometry, in particular the roundness. The yarn or rope 10 is shown in cross-section in FIG. 12 and three image sensors 41, 42, 43 with a mutual angular spacing of 120° are arranged round the yarn or rope. Each image sensor is formed in the manner explained with reference to FIG. 1 for the image sensor 12 and connected to a signal processing circuit of the type described. With the aid of the three image sensors 41, 42, 43 three two-dimensional images of the yarn or rope are obtained and the digitized image signals are stored. If the three diameters $D_1$, $D_2$ and $D_3$ of the yarn or rope are measured in these three views then from the differences of these three diameters a measure of the unroundness can be derived:

$$unroundness = f(|D_1-D_2|, |D_2-D_3|, |D_3-D_1|)$$

Other modifications and further developments of the arrangement described are of course possible. In particular, instead of the grey value images colour images may be taken, stored and evaluated. The technology necessary for this is known to the expert in particular from colour television. Instead of the pure brightness values of the image the intensity values of the three colour components of each image point are digitized and stored. By suitable evaluation of the colour signals, possibly also by intentional incorrect-colour formers, it is then possible either to detect the aforementioned measured values more clearly or to obtain additional information on other properties of the yarn or rope.

I claim:

1. A method of measuring and/or monitoring properties of a yarn or rope comprising the steps of:
   (a) taking a two-dimensional image of a portion of the yarn or rope using an image sensor which converts the image to electrical image signals;
   (b) digitizing the image signals to provide digital image signals each of which corresponds to an image point of the image;
   (c) storing the digital image signals in an image signal memory for which each image point of the two-dimensional image has a memory location at which the complete digital image signal of the respective image point can be stored; and
   (d) determining the number of twists per unit length or the length of a twist of the yarn or rope from the stored digital image signals using a calculating unit by determining the period of the structure of the yarn or rope in an evaluation direction which is parallel to the longitudinal direction of the yarn or rope.

2. A method according to claim 1 wherein said determining step further comprises calculating using the calculating unit a unidimensional similarity function of stored digital image signals corresponding to image points of at least one image point row extending in the evaluation direction and determining the period o the structure of the yarn or rope from the unidimensional similarity function.

3. A method according to claim 2 wherein said determining step further comprises calculating the auto-correlation function as the unidimensional function, and determining the period of the structure of the yarn or rope from the distance between two or more consecutive maxima of the auto-correlation function.

4. A method according to claim 2 wherein said determining step further comprises calculating the difference function as the unidimensional function, the difference function representing the sums of the quantity differences of stored digital image signals corresponding to image points of at least one image point row extending in the evaluation direction, and determining the period of the structure of the yarn or rope from the distance between two or more minima of the difference function.

5. A method according to claim 2 wherein said determining step further comprises calculating a spectral transform of the two-dimensional image from the stored image signals and determining the period of the structure of the yarn or rope from the dominant maximum of the spectrum.

6. A method of measuring and/or monitoring properties of a yarn or rope comprising the steps of:
   (a) taking a two-dimensional image of a portion of the yarn or rope using an image sensor which converts the image to electrical image signals;
   (b) digitizing the image signals to provide digital image signals each of which corresponds to an image point of the image;
   (c) storing the digital image signals in an image signal memory which for each image point of the two-dimensional image has a memory location at which the complete digital image signal of the respective image point can be stored; and
   (d) determining the mean fibre angle of the individual fibres of the yarn or rope from the stored digital image signals using a calculating unit.

7. A method according to claim 6 wherein said determining step comprises calculating the cross-ecorrelation function of stored digital image signals which originate from two spaced-apart image point rows extending parallel to an evaluation direction and determining the mean fibre angle from the maximum of the cross-correlation function.

8. A method according to claim 6 wherein said determining step further comprises determining the mean fibre angle by a Hough transformation.

9. A method according to claim 8 further comprising the steps of:
   (e) binarizing the stored digital image signals so that the image points of the image of the yarn or rope, depending on their brightness values, become either white or black;
   (f) determining a plurality of straight lines each of which is common to a large number of white image points of a selected image fragment by a Hough transformation performed by the calculating unit with the binarized digital image signals;
   (g) determining the angle of inclination of each of the straight lines with respect to the longitudinal axis of the yarn or rope, wherein the angle of inclination corresponds to a probable fibre angle; and
   (h) forming a histogram of the frequency distribution of the angles of inclination of the straight lines and determining the mean fibre angle from the maximum of the histogram.

10. A method according to claim 9, wherein the digitally stored image is differentiated in several directions for emphasizing the edges before determining the mean fibre angle by a Hough transformation.

11. A methd according to claim 6 wherein said determining step comprises determining the mean fibre angle by vector rotation.

12. A method according to claim 11 further comprising the steps of:
   (e) binarizing the stored digital image signals so that the image points of the image of the yarn or rope, depending on their brightness values, become either white or black;

(f) rotating a vector in predetermined angular steps through the image of the yarn or rope and for each angular position of the vector counting the white image points lying on the vector;

(g) forming a histogram of the number of white image points obtained for each angular position of the vector; and (h) determining the mean fibre angle from the maximum of a sum histogram of the results obtained from a plurality of measurements carried out over the entire image of the yarn or rope.

13. A method according to claim 12 wherein the digitally stored image is differentiated in several directions for emphasizing the edges before determining the mean fibre angle by vector rotation.

14. A method of measuring and/or monitoring properties of a yarn or rope comprising the steps of:
(a) taking a two-dimensional image of a portion of the yarn or rope using an image sensor which converts the image to electrical image signals;
(b) digitizing the image signals to provide digital image signals each of which corresponds to an image point of the image;
(c) storing the digital image signals in an image signal memory which for each image point of the two-dimensional image has a memory location at which the complete digital image signal of the respective image point can be stored; and
(d) determining the diameter of the yarn or rope from the stored digital image signals using a calculating unit by counting the number of image points belonging to the image of the yarn or rope along one or more lines extending transversely of the longitudinal axis of the yarn or rope.

15. A method of measuring and/or monitoring properties of a yarn or rope comprising the steps of:
(a) taking a two-dimension image of a portion of the yarn or rope by using an image sensor which converts the image to electrical image signals;
(b) digitizing the image signals to provide digital image signals each of which corresponds to an image point of the image;
(c) storing the digital image signals in an image signal memory which for each image point of the two-dimensional image has a memory location at which the complete digital image signal of the respective image point can be stored; and
(d) determining the diameter of the yarn or rope from the stored digital image signals using a calculating unit by determining the ratio of the total number of image points belonging to the image of the yarn or rope to the total number of the image points of the two-dimensional image.

16. A method of measuring and/or monitoring properties of a yarn comprising the steps of:
(a) taking a two-dimensional image of a portion of the yarn or rope using an image sensor which converts the image to electrical image signals;
(b) digitizing the image signals to provide digital image signals each of which corresponds to an image point of the image;
(c) storing the digital image signals in an image signal memory which for each image point of the two-dimensional image has a memory location at which the complete digital image signal of the respective image point can be stored; and
(d) determining statistical values of projecting filaments or wires from the stored digital image signals using a calculating unit by counting the image points belonging to the projecting filaments or wires in one or more test strips extending parallel to the image of the yarn or rope.

17. A method according to claim 16 wherein each test strip corresponds to an image point row.

18. A method according to claim 16 wherein each test strip corresponds to several adjacent image point rows.

19. A method of measuring and/or monitoring properties of a yarn or rope comprising the steps of:
(a) taking two or more two-dimensional images of a portion of the yarn or rope from different angles using image sensors which convert the images to electrical image signals;
(b) digitizing the image signals to provide digital image signals each of which corresponds to an image point of the images;
(c) storing the digital image signals in an image signal memory which for each image point of the two-dimensional images has a memory location at which the complete digital image signal of the respective image point can be stored;
(d) determining the diameter of the yarn or rope from the stored digital image signals of each two-dimensional image using a calculating unit; and
(e) determining the unroundness of the yarn or rope using the calculating unit by comparing the diameters obtained for the different two-dimensional images.

20. A method according to claim 19 wherein said determining the diameter step further comprises determining each diameter of the yarn or rope by counting the number of image points belonging to the image of the yarn or rope along one or more lines extending transversely of the longitudinal axis of the yarn or rope.

21. A method according to claim 19 wherein said determining the diameter step further comprises determining each diameter of the yarn or rope by determining the ratio of the total number of image points belonging to the image of the yarn or rope to the total number of the image points of the two-dimensional image.

* * * * *